United States Patent [19]

Minagawa et al.

[11] 4,371,647
[45] Feb. 1, 1983

[54] 2,6-DI-TERTIARY BUTYL PHENYL PENTAERYTHRITOL SPIRO BIS-PHOSPHITES ENHANCING THE STABILITY TO HEAT AND LIGHT OF SYNTHETIC RESIN

[75] Inventors: Motonobu Minagawa, Kosigaya; Yutaka Nakahara, Iwatsuki; Etsuo Tobita, Tokyo, all of Japan

[73] Assignee: Adeka Argus Chemical Co. Ltd., Urawa, Japan

[21] Appl. No.: 223,051

[22] Filed: Jan. 7, 1981

[30] Foreign Application Priority Data

Apr. 28, 1980 [JP] Japan ................... 55-56594

[51] Int. Cl.³ .............. C07F 9/15; C08K 5/52; C09K 15/32
[52] U.S. Cl. .............. 524/120; 252/400 A; 260/927 R; 524/101; 524/291; 524/342; 524/350
[58] Field of Search ............... 260/45.7 PH, 45.8 R, 260/45.8 TH, 45.85 R, 927 R; 525/132, 133, 146, 394; 524/120; 252/400 A

[56] References Cited

U.S. PATENT DOCUMENTS

| | | | |
|---|---|---|---|
| 3,039,993 | 6/1962 | Friedman | 260/45.95 H |
| 3,231,531 | 1/1966 | Buckley et al. | 260/45.75 W |
| 3,281,506 | 10/1966 | Shepard et al. | 260/967 |
| 3,723,427 | 3/1973 | Susi | 260/45.8 TH |
| 3,956,361 | 5/1976 | Stephen | 260/45.85 B |
| 3,963,804 | 6/1976 | Yonemitsu et al. | 260/45.7 PH |
| 4,066,611 | 1/1978 | Axelrod | 260/45.8 R |
| 4,094,855 | 6/1978 | Spivack | 524/120 |
| 4,102,859 | 7/1978 | Elmers et al. | 106/177 |
| 4,105,627 | 8/1978 | Sekiguchi et al. | 260/45.7 PH |
| 4,107,136 | 8/1978 | Minagawa et al. | 525/146 |
| 4,221,700 | 9/1980 | Minagawa et al. | 260/45.7 PH |
| 4,305,866 | 12/1981 | York et al. | 260/45.8 R |

*Primary Examiner*—John Kight, III
*Assistant Examiner*—R. A. White

[57] ABSTRACT

2,6-Di-tertiary butyl phenyl pentaerythritol spiro bis-phosphites are provided having the structure:

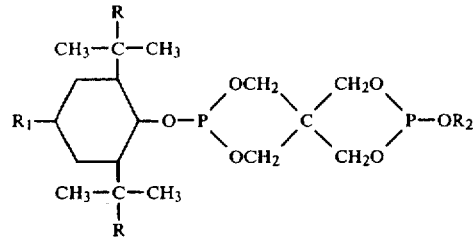

wherein:
R is alkyl having from one to six carbon atoms;
$R_1$ is methyl or ethyl;
$R_2$ is selected from the group consisting of alkyl having from one up to about eighteen carbon atoms; cycloalkyl having from three up to about twelve carbon atoms; and alkaryl and aryl having from six to about thirty carbon atoms; such groups substituted with from one to about four oxy ether—O— and/or carboxylic ester—COO—groups; the residue of a polyhydric alcohol having from two to about eighteen carbon atoms, and from two to about ten hydroxyl groups; and the residue of a polyphenol having from six to about eighteen carbon atoms and from two to about ten phenolic hydroxyl groups.

Stabilizer compositions are provided comprising a phenolic antioxidant and such phosphites as well as synthetic resin compositions having an enhanced resistance to deterioration by heat and/or light due to the presence of such a phosphite and/or stabilizer composition.

51 Claims, No Drawings

2,6-DI-TERTIARY BUTYL PHENYL PENTAERYTHRITOL SPIRO BIS-PHOSPHITES ENHANCING THE STABILITY TO HEAT AND LIGHT OF SYNTHETIC RESIN

Polypropylene and other polyolefins such as polyethylene, polybutylene and polyisopentylene show a strong tendency to deteriorate in physical properties at elevated temperatures and when exposed to ultraviolet light. The deterioration is evidenced by, among other things, a decrease in viscosity, a tendency to become brittle, and a discoloration which is particularly pronounced at the exposed edge of the material. This deterioration can be accompanied by distortion, cracking, and powdering of the material. The deterioration is accentuated in the presence of oxygen.

To overcome these difficulties, many stabilizer systems have been proposed for combination with polyolefins, with varying degrees of success. No single stabilizer has proved adequate, and combinations of stabilizers are consequently used almost exclusively. Most stabilized polyolefins on the market contain one or more of such stabilizer combinations. The deterioration appears to be due to a combination of factors, and a combination of stabilizers is therefore more capable of coping with the various types of deterioration. However, the retention of good physical properties over long periods of time remains rather difficult to achieve.

Of the many stabilizer systems that have been proposed, one particularly satisfactory stabilizer system is described in U.S. Pat. No. 3,255,136, patented June 7, 1966 to Arthur Hecker, Otto S. Kauder and Norman Perry. This stabilizer system comprises three stabilizers: an organic mono- or polyhydric phenol, an organic phosphite, and a thiodipropionic acid ester. An additional fourth ingredient, which is preferred but not essential, is a polyvalent metal salt of an organic acid. These three and four stabilizers together give an enhanced stabilization which is not obtainable from any of them alone, or in combinations of two.

In these combinations, the phenol alone gives an improved resistance to embrittlement and reduction in melt viscosity of polypropylene at elevated temperatures, but little assistance as to maintenance of color. The phosphite alone is a rather poor stabilizer in preventing deterioration in the first two properties, but it does assist in resisting discoloration. The two together are worse than the phenol alone in every respect except color, which is intermediate.

The thiodipropionic acid ester by itself only improves resistance to embrittlement. The polyvalent metal salt of an organic acid by itself only prevents discoloration. In combinations with the phenol, the color is worse than with the salt alone, and combinations with phosphite only, discoloration is prevented. The effectiveness of all three or four ingredients taken together against all of these types of deterioration is therefore particularly surprising.

The organic phosphite can be any organic phosphite having the formula $(RA)_3$—$P$, in which A can be oxygen or sulfur or a mixture of the same, and R is aryl, alkyl, cycloalkyl, aralkyl or aralkaryl in any combination. A variety of tris-alkaryl phosphites are disclosed, such as tris-(tertiary-octyl-phenyl) phosphite and tris-(tertiary-nonyl-phenyl) phosphite, but no tris-(alkaryl) phosphites having more than one alkyl group per phenyl group.

Organic phosphites have been widely used as stabilizers for polyolefins and similar polymeric materials, and many different types of phosphites, some of rather complex structure, have been proposed. U.S. Pat. Nos. 3,255,136 and 3,655,832 have suggested organic phosphite-phenol transesterification products, the preferred phenol being a bis-phenol. Other types of tris-(alkaryl) phosphite esters have been disclosed in U.S. Pat. Nos. 2,220,113; 2,220,845; 2,246,059; 2,419,354; 2,612,488; 2,732,365; 2,733,226; and 2,877,259. Additional tris-(alkaryl) phosphites are disclosed in U.S. Pat. No. 3,167,526 to Nicholson, patented Jan. 26, 1965; No. 3,061,583 to Huhn and Sheets, patented Oct. 30, 1962; No. 3,829,396 to Oakes and Cross, patented Aug. 13, 1974; French Pat. Nos. 1,496,563 to U.S. Rubber Company, délivré Aug. 21, 1967, and 1,497,390 to Ethyl Corporation, délivré Aug. 28, 1967; and British Pat. Nos. 1,058,977, published Feb. 15, 1967, to Hooker Chemical Corporation and 1,143,375, published Feb. 19, 1969, to Uniroyal Inc.

Oakes et al disclose bis-(2,4-di-tertiary-butyl-phenyl) cyclohexyl phosphite and 2,4-di-(tertiary butyl) phenyl dicyclohexyl phosphite, which are liquids.

French Pat. No. 1,496,563 described phosphites derived from 2,6-di-tertiary-butyl-hydroquinone and 2,5-di-tertiary-butyl-hydroquinone, and it is suggested that they can be used with thiodipropionic acid esters of olefin polymers.

British Pat. No. 1,143,375 has a similar disclosure; tris-(2,5-di-tertiary-butyl-4-hydroxy-phenyl)phosphite is disclosed.

British Pat. No. 1,058,977 discloses 2,4,6-tri-substituted aryl phosphites, the substituents including tertiary-butyl groups.

French Pat. No. 1,497,390 discloses tris-(3,5-di-alkyl-4-hydroxy-phenyl)phosphites, as well as tris-(3-isopropyl-5-tertiary-butyl-phenyl)phosphite.

Kuriyama et al U.S. Pat. No. 3,558,554 patented Jan. 26, 1971, provides olefin polymer compositions containing as a stabilizer an organophosphite having the general formula:

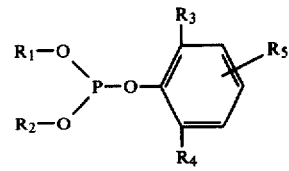

wherein $R_1$ and $R_2$ each represents a member selected from the group consisting of substituted and unsubstituted alkyl, cycloalkyl, aryl, alkaryl, aralkyl, and aliphatic thio ether groups and $R_3$, $R_4$ and $R_5$ each represents a member selected from the group consisting of hydrogen and alkyl, cycloalkyl, aryl, alkaryl, and aralkyl groups, at least one of said $R_3$ and $R_4$ being a tertiary butyl group.

Suitable organo phosphites include, for example, di-n-butyl (2-t-butyl-cresyl)phosphite, di-n-hexyl(2-t-butyl-m-cresyl)phosphite, di-n-hexyl(2-t-butyl-p-cresyl)phosphite, di-n-octyl(2-t-butyl-p-cresyl)phosphite, di-n-butyl-3,4-di-t-butyl-phenyl)phosphite, di-n-butyl-(2,6-di-t-butyl-p-cresyl)phosphite, di-phenyl (2-t-butyl-p-cresyl)phosphite, tri-(2-t-butyl-p-cresyl)-phosphite, di-(ethylthioethyl)-(2-t-butyl-p-cresyl)-phosphite, di(octylthioethyl) (2-t-butyl-p-cresyl)-phosphite, and tri(2,4-di-t-butyl-phenyl)phosphite.

Many organic phosphites have been proposed as stabilizers for polyvinyl chloride resins, and are employed either alone or in conjunction with other stabilizing compounds, such as polyvalent metal salts of fatty acids and alkyl phenols. Such phosphite stabilizers normally contain alkyl or aryl radicals in sufficient number to satisfy the three valences of the phosphite, and typical phosphites are described in the patent literature, for example, W. Leistner et al., U.S. Pat. Nos. 2,564,646 of Aug. 14, 1951, 2,716,092 of Aug. 23, 1955, and 2,997,454 of Aug. 2, 1961.

Organic phosphites have also been added as stabilizers in amounts of 0.01 to 1%, preferably 0.05% to 0.2% by weight, to high molecular weight polycarbonate plastics, for example the polycarbonate of 2,2'-bis(4-hydroxyphenyl)propane of molecular weight 10000 and up to over 50000 as disclosed by G. Fritz in U.S. Pat. No. 3,305,520 of Feb. 21, 1967.

A. Hecker in U.S. Pat. No. 2,860,115 of Nov. 11, 1958 discloses compositions of organic phosphites with metal salts of carboxylic acids used in olefin polymers.

Phosphites are also employed in conjunction with other stabilizers such as a polyhydric phenol in the stabilization of polypropylene and other synthetic resins against degradation upon heating or ageing under atmospheric conditions. The polyhydric phenol is thought to function as an antioxidant in such combinations. Disclosures by R. Werkheiser, U.S. Pat. Nos. 2,726,226 of Dec. 6, 1975; I. Salyer et al, 2,985,617 of May 23, 1961; L. Friedman, 3,039,993 of June 19, 1962; W. Nudenberg, 3,080,338 of Mar. 5, 1963; C. Fuchsman, 3,082,187 of Mar. 19, 1963; H. Orloff et al, 3,115,465 of Dec. 24, 1963; A. Nicholson, 3,167,526 of Jan. 26, 1965; A. Hecker et al, 3,149,093 of Sept. 15, 1964, 3,244,650 of Apr. 5, 1966 and 3,225,136 and 3,255,151 of June 7, 1966; C. Bawn, 3,352,820 of Nov. 14, 1967; D. Miller, 3,535,277 of Oct. 20, 1970; J. Casey, 3,586,657 of June 2, 1971; C. Abramoff 3,856,728 of Dec. 24, 1974; M. Minagawa, 3,869,423 of Mar. 4, 1975 and 3,907,517 of Sept. 23, 1975; and British Pat. Nos. 846,684, 851,670, and 866,883 are representative of stabilizer combinations including organic phosphites, polyhydric phenols, and other active ingredients.

The importance of organic phosphites as stabilizers for synthetic resins has led to the development of a large variety of special phosphites intended to provide improved stabilizing effectiveness and compatibility and ease of compounding with the resin and with other stabilizers commonly used. However, the phosphites which have been proposed have not been entirely successful, partly because of their complicated structure, which makes them costly to prepare, and partly because of their difficulty of preparation.

Among these special phosphites, L. Friedman, U.S. Pat. No. 3,047,608 of July 31, 1962 discloses a class of biphosphites having the formula:

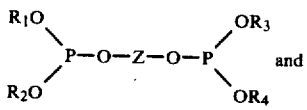

and

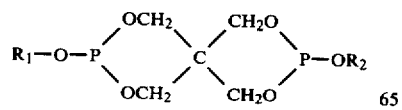

in which $R_1$, $R_2$, $R_3$ and $R_4$ are alkyl or aryl and Z is $-CH_2CH_2SCH_2CH_2O-$, $-C_2CH_2SO_2C_2C-$ $H_2-(-CH_2CH_2O-)_x$ or $(CHCH_3CH_2)_x$ where x is at least two, and in U.S. Pat. No. 3,053,878 of Sept. 11, 1962 a class of linear phosphite polymers having the formula:

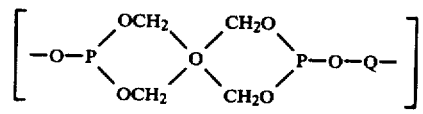

in which Q is the alkylene or arylene portion of a dihydric alcohol or dihydric phenol.

R. Morris et al in U.S. Pat. No. 3,112,286 of Nov. 26, 1963 discloses phosphites having the formula:

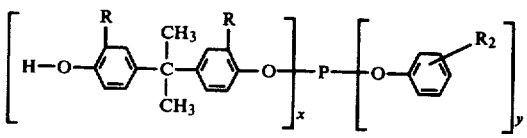

in which

R represents a bulky hydrocarbon group such as t-butyl, t-amyl, t-hexyl, cyclohexyl, t-pentyl, t-octyl, phenyl and the like;

$R_1$ represents hydrogen and R;

$R_3$ represents an alkyl group from six to twenty carbon atoms which is preferably in the meta or para position;

x represents a number of from 1 to 3 inclusive;

y represents a number of from 0 to 2 inclusive and the sum of the numerical value of x+y is always exactly 3.

D. Brown, U.S. Pat. No. 3,297,631 of Jan. 10, 1967 discloses condensation products of phosphorus compounds with bisphenols and trisphenols which may be represented by the structures:

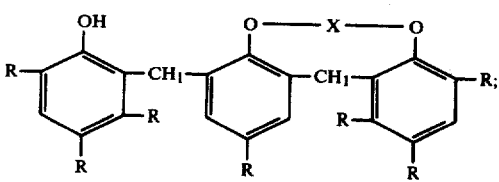

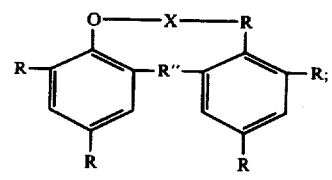

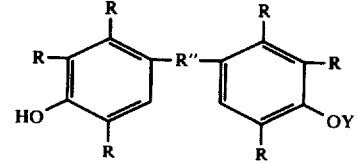

where: X is selected from the following: $>P-OR'$; $>P-R'$;

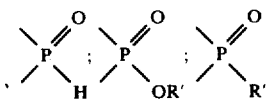

and Y is selected from the following: —P(OR')$_2$;

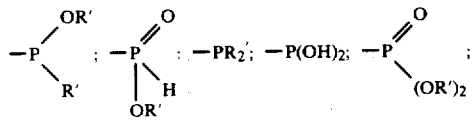

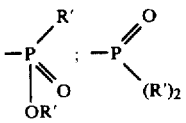

R is hydrogen, alkyl of one to sixteen carbon atoms or aryl or a combination of these; R' is alkyl of one to sixteen carbon atoms or aryl, and R" is alkylidene of one to sixteen carbon atoms or an aryl-substituted alkylidene.

C. Baranauckas, U.S. Pat. No. 3,305,608 of Feb. 21, 1967, discloses phenolic phosphites useful as polymer stabilizers prepared by reacting a triorganophosphite, a polyol, and an aromatic material having two to six phenolic hydroxyl groups at 60° to 180° C. in specified proportions.

C. Brindell, U.S. Pat. No. 3,412,064 of Nov. 19, 1968 discloses phenolic phosphites represented by the general formula:

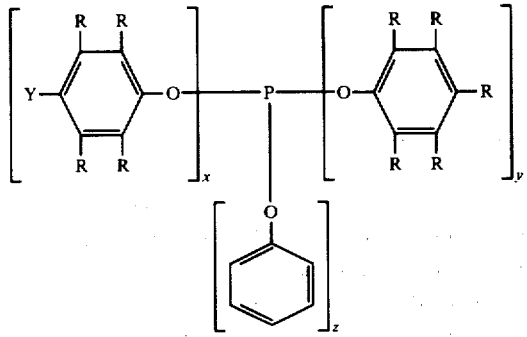

where x is from 1 to 3, y and z each from 0 to 2, $x+y+z=3$, R is hydrogen or alkyl and Y is hydroxyl or a group of the formula:

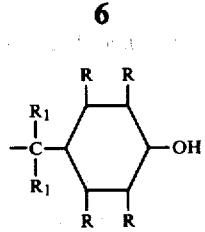

where R is hydrogen or alkyl.

M. Larrison, U.S. Pat. No. 3,419,524 of Dec. 31, 1968, discloses phosphites useful as polymer stabilizers having the formula:

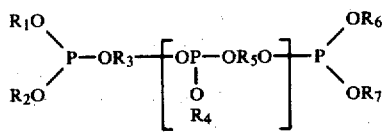

where $R_1$, $R_2$, $R_4$, $R_6$ and $R_7$ are aryl or haloaryl, and $R_3$ and $R_5$ are a polyalkylidene glycol or an alkylidene bisphenol or a hydrogenated alkylidene bisphenol or a ring-halogenated alkylidene bisphenol from which the two terminal hydrogens have been removed.

O. Kauder et al, U.S. Pat. No. 3,476,699 of Nov. 4, 1969 and No. 3,655,832 of Apr. 11, 1972 discloses organic phosphites containing a free phenolic hydroxyl group and defined by the formula:

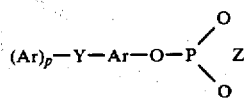

wherein Z is selected from the group consisting of hydrogen and aliphatic, cycloaliphatic, aromatic, heterocyclic and (Ar)$_p$—Y—Ar groups, taken in sufficient number to satisfy the valences of the two phosphite oxygen atoms; Y is a polyvalent linking group selected from the group consisting of oxygen; aliphatic, cycloaliphatic and aromatic hydrocarbon groups attached to each Ar group through a carbon atom not a member of an aromatic ring; oxyaliphatic; thioaliphatic, oxycycloaliphatic, thiocycloaliphatic; heterocyclic, oxyheterocyclic, thioheterocyclic, carbonyl, sulfinyl; and sulfonyl groups; Ar is a phenolic nucleus which can be phenyl or a polycarbocyclic group having condensed or separate phenyl rings; each Ar group is either connected through an oxygen atom to a phosphite group or contains a free phenolic hydroxyl group, or both; and p is a number, one or greater, and preferably from one to four, which defines the number of Ar groups linked to Y.

L. Friedman, U.S. Pat. No. 3,516,963 of June 23, 1970 discloses phosphites having th formula:

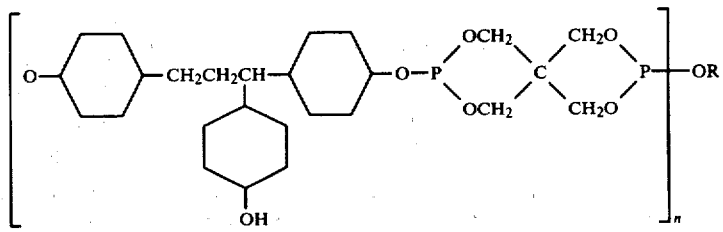

where R is alkyl, alkenyl, aryl, aralkyl, haloaryl, haloalkyl or

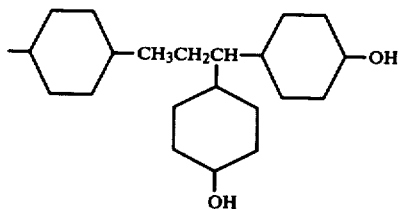

and n is an integer of at least 1. n can be 2, 3, 4, 5, 6, 7, 8, 10, 50, 100 or even more.

D. Bown et al in U.S. Pat. Nos. 3,510,507 of May 5, 1970 and 3,691,132 of Sept. 12, 1972 discloses polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula:

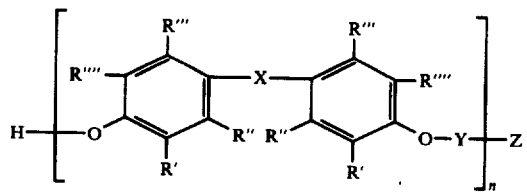

where X is selected from the group consisting of

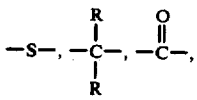

—C—C, and C—A—C— where A is a $C_1$ to $C_{16}$ alkylene or an arylene; R', R", R''', and R'''' are selected from the group consisting of hydrogen, $C_1$ to $C_{18}$ alkyls, and an aryl group; Y is selected from the group of

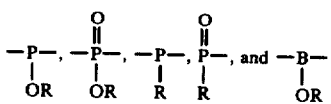

where R is hydrogen, a $C_1$ to $C_{18}$ alkyl or aryl;

where m is 0 to 10, preferably 4 to 8,

where A' is $(CH_2)_n$—S—$(CH_2)_n$ or —$(CH_2)_n$—S—$(CH_2)_m$—S—$(CH_2)_n$ where n is 0 to 10, preferably 2 and m is 0 to 10, preferably 5;

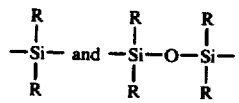

where R is an alkyl, preferably methyl, and Z is

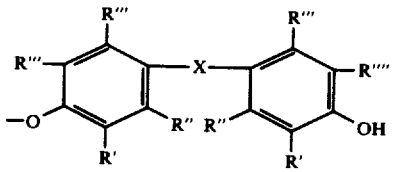

where R', R", R''', R'''', and X correspond respectively to the R', R", R''', R'''', and X previously selected when n has a value from 1 to 15, or may be derived from the compound used to introduce Y into the product when n has a value from 2 to 15, for example, —R or —OR where R is hydrogen, an alkyl, or aryl. When Y is the formula of Bown's stabilizer is

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto) paraxylylene, and 10,24-dithiotetracontane.

J. Floyd et al in German published application No. 2505071 of Aug. 14, 1975 abstracted in Chemical Abstracts 1976, Volume 84, abstract No. 5945f, discloses low molecular weight polycarbonate esters of bisphenols such as 2,2-bis(3-t-butyl-4-hydroxyphenylpropane) and 4,4'-butylidene bis(6-t-butyl-3-methylphenol) prepared in such a way as to contain few or no free phenolic hydroxyl groups as being highly effective heat and light stabilizers for polyolefins and giving a synergistic effect with distearyl thiodipropionate, tris (nonylphenyl) phosphite, and distearyl pentaerythritol diphosphite.

In accordance with the present invention, there are provided 2,6-di-tertiary-butyl phenyl pentaerythritol spiro bisphosphites having the general structure:

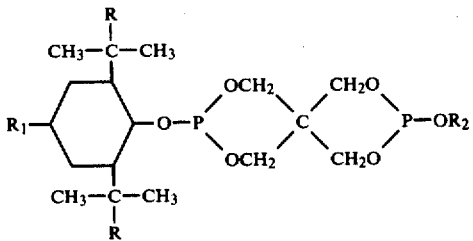

wherein:

R is alkyl having from one to six carbon atoms;

$R_1$ is methyl or ethyl;

$R_2$ is selected from the group consisting of alkyl having from one up to about eighteen carbon atoms; cycloalkyl having from three up to about twelve carbon atoms; and alkaryl and aryl having from six to about thirty carbon atoms; such groups substituted with from one to about four oxy ether-O- and/or carboxylic ester-COO-groups; the residue of a polyhydric alcohol having from two to about eighteen carbon atoms, and from two to about ten hydroxyl groups; and the residue of a polyphenol having from six to about eighteen carbon atoms and then two to about ten phenolic hydroxyl groups.

Stabilizer compositions are provided comprising a phenolic antioxidant and such phosphites as well as synthetic resin compositions having an enhanced resistance to deterioration by heat and/or light due to the presence of such a phosphite and/or stabilizer composition.

These phosphites and stabilizer compositions are capable of enhancing the resistance to deterioration due to heat and/or light of synthetic resins as a class, when combined therewith in small amounts, within the range from about 0.01 to about 5% of the phosphite and from about 0.01 to about 10% of the stabilizer composition, by weight of the synthetic resin.

Exemplary R and $R_2$ alkyl groups include, for example, methyl, ethyl, propyl, isopropyl, butyl, secondary butyl, tertiary butyl, isobutyl, amyl, isoamyl, secondary amyl, 2,2-dimethyl propyl, tertiary amyl, hexyl, isohexyl, heptyl, octyl, 2-ethyl hexyl, isooctyl, nonyl, isononyl, decyl, isodecyl, lauryl, myristyl, palmityl, stearyl, eicosyl and behenyl.

R and $R_2$ may also be cycloalkyl having about three to about twelve carbon atoms, including, for example, cyclopropyl, cyclobutyl, cyclopentyl, cyclohexyl, cycloheptyl, cyclooctyl, cyclododecyl and alkyl-substituted cycloalkyl such as 4-methyl cyclohexyl, 4-methyl cyclopentyl, and p-dimethyl cyclohexyl.

R and $R_2$ alkaryl and aryl groups include phenyl, diphenyl, naphthyl, tolyl, xylyl, ethylphenyl, butylphenyl, tertiary butylphenyl, octylphenyl, 2,6-di-t-butyl-4-methylphenyl, 2,6-di-t-butyl-4-methoxycarbonyl ethylphenyl, isooctylphenyl, t-octylphenyl, nonylphenyl, 2,4-di-t-butylphenyl, cyclohexylphenyl, cyclooctylphenyl, 4-methoxyphenyl, 4-ethoxyphenyl, 3-lauroxyphenyl, 2-methoxy-4-methylphenyl, 2-t-butyl-4-methoxyphenyl, 4-benzyloxyphenyl, and 3,4-methylenedioxyphenyl.

Examples of R and $R_2$ alkyl and alkaryl including ether and carboxylic acid ester groups include 2,6-di-t-butyl-4-methoxycarbonyl ethylphenyl, 4-methoxyphenyl, 4-ethoxyphenyl, 3-lauroxyphenyl, 2-methoxy-4-methylphenyl, 2-t-butyl-4-methoxyphenyl, 4-benzyloxyphenyl, and 3,4-methylenedioxyphenyl.

R and $R_2$ can also be the residue of a polyhydric alcohol or polyphenol having at least two up to about ten alcoholic or phenolic hydroxyl groups capable of being esterified with trivalent phosphorous of a phosphite, of which at least one such group is taken up by phosphorus and the remaining group or groups may be taken up with phosphorus or may be free, such as, for example, ethylene glycol, glycerol, erythritol, pentaerythritol, sorbitol, mannitol, dulcitol, trimethylol ethane, trimethylol propane, trimethylol butane, 1,2-propanediol, 1,3-propanediol, 1,2-butanediol, 1,4-butanediol, neopentylglycol, thiodiethyleneglycol, 1,6-hexanediol, 1,10-decanediol, 1,4-cyclohexanediol, 1,4-cyclohexanedimethanol, 1,4- phenylenedimethanol, hydrogenated Bisphenol A, glycerine, trimethylolethane, trimethylolpropane, tris(2-hydroxyethyl) isocyanurate.

Also included are the polyoxyalkylene polyols containing one or more oxyalkylene groups with terminal hydroxyls free or etherified with alkyl, cycloalkyl or phenyl groups having from one to about ten carbon atoms, Exemplifying this class are methyl Cellosolve, ethyl Cellosolve, isopropyl Cellosolve, butyl Cellosolve, hexyl Cellosolve, cyclohexyl Cellosolve, and phenyl Cellosolve; methyl Carbitol, ethyl Carbitol, isopropyl Carbitol, butyl Carbitol and isobutyl Carbitol; dipropylene glycol, diethylene glycol, triethylene glycol, triethylene glycol monomethyl ether, triethylene glycol monoethyl ether, triethylene glycol monobutyl ether, glyceryl 1,2-dimethyl ether, glyceryl,1,3-dimethyl ether, glyceryl 1,3-diethyl ether and glyceryl 1-ethyl-2- propyl ether; nonyl phenoxy; polyethoxy ethyl, and lauroxy polyethoxyethyl.

Exemplary polyhydric phenol residues include hydroquinone, 2,5-di-t-butylhydroquinone, 2,3,6-trimethylhydroquinone, 2-methylresorcinol, 2,6-di-t-butylresorcinol, 2,2'-methylenebis (4-methyl-6-t-butylphenol), 2,2'-methyleneis(4-ethyl-6-t-butylphenol), 2,2'-methylenebis[4-methyl-6-(α-methylcyclohexyl) phenol], 2,2'-n-butylidenebis(4,6-dimethylphenyl), 1,1-bis-(2'-hydroxy-3',5'-dimethylphenyl)-3,5,5-trimethylhexane, 2,2'- cyclohexylidenebis(4-ethyl-6-t-butylphenol), 2,2'-thiobis(4-t-butyl-6-methylphenol), 2,2'-isopropylidene bis(4-t-butyl-6-methylphenol), 1,4-benzylidenebis(4-ethyl-6-t-butylphenol), 2,2'-thiobis(4-methyl-6-t-butylphenol), 2,2'-thiobis(4,6-di-t-butylphenol), 4,4'-methylene bis(2-methyl-6-t-butylphenol), Bisphenol A, 4,4'-isopropylidenebis (2-phenylethylphenol), 4,4'-n-butylidenebis(3-methyl-6-t-butylphenol), 4,4'-cyclohexylidenebisphenol, 4,4'-cyclohexylidenebis (2-t-butyl-phenol), 4,4'-cyclohexylidenebis(2-cyclohexylphenol), 4,4'-benzylidenebis(2-t-butyl-5-methylphenol), 4,4'-oxabis(3-methyl-6-isopropylphenol), 4,4'-thiobis(3-methyl-6-t-butylphenyl), 4,4'-sulfobis(3-methyl-6-t-butylphenol), bis(2-methyl-4-hydroxy-5-t- butylbenzyl)sulfide, and 1,1,3-tris(2'-methyl-4'-hydroxy-5'-t-butylphenyl)butane.

Exemplary 2,6-di-t-butylphenyl pentaerythritol spiro bisphosphites useful with phenolic antioxidants in accordance with the invention include 2,6-di-t-butyl-4-methylphenyl phenyl pentaerythritol diphosphite, 2,6-di-t-butyl-4-methylphenyl methyl pentaerythritol diphosphite, 2,6-di-t-butyl-4-methylphenyl-2-ethylhexyl pentaerythritol diphosphite, 2,6-di-t-butyl-4-methylphenyl isodecyl pentaerythritol diphosphite, 2,6-di-t-butyl-4-ethylphenyl lauryl pentaerythritol diphosphite, 2,6-di-t-butyl-4-ethylphenyl isotridecyl pentaerythritol diphosphite, 2,6-di-t-butyl-4-methylphenyl stearyl pentaerythritol diphosphite, 2,6-di-t-butyl-4-methylphenyl cyclohexyl pentaerythritol diphosphite, 2,6-di-t-butyl-4-ethylphenyl benzyl pentaerythritol diphosphite, 2,6-di-t-butyl-4-methylphenyl ethylcellosolve pentaerythritol diphosphite, 2,6-di-t-butyl-4-methylphenyl butylcarbitol pentaerythritol diphosphite, 2,6-di-t-butyl-4-methylphenyl octylphenyl pentaerythritol diphosphite, 2,6-di-t-butyl-4-methylphenyl nonylphenyl pentaerythritol diphosphite, bis(2,6-di-t-butyl-4-methylphenyl) pentaerythritol diphosphite, bis(2,6-di-t-butyl-4-ethylphenyl) pentaerythritol diphosphite, 2,6-di-t-butyl-4-methylphenyl-2,6-di-t-butylphenyl pentaerythritol diphosphite, 2,6-di-t-butyl-4-methylphenyl-2,4-di-t-butylphenyl pentaerythritol diphosphite, 2,6-di-t-butyl-4-methylphenyl-2,4-di-t-octylphenyl pentaerythritol diphosphite, 2,6-di-t-butyl-4-methylphenyl-2-cyclohexylphenyl pentaerythritol diphosphite, 2,6-di-t-amyl-4-methylphenyl phenyl pentaerythritol diphosphite, bis(2,6-di-t-amyl-4-methylphenyl) pentaerythritol diphosphite, bis(2,6-di-t-octyl-4-methylphenyl) pentaerythritol diphosphite.

These phosphites are readily prepared by conventional procedures. Thus, for example, the corresponding 2,6-di-t-butyl-4-methyl or ethyl phenol can be reacted with phosphorus trichloride or a triphosphite such as trimethyl phosphite or triphenyl phosphite, pentaerythritol, and $R_2OH$ in the presence of a base, such as an amine catalyst, to form the phosphite.

The following Example serves to illustrate the procedure:

EXAMPLE I

Synthesis of bis(2,6-di-t-butyl-4-methylphenyl) pentaerythritol diphosphite 2,6-Di-t-butyl-4-methylphenol 11.02 g (0.05 mole) and triethylamine 6.1 g (0.06 mole) were dissolved in 50 ml of chloroform and the $PCl_3$ 6.88 g (0.05 mole) was added dropwise at room temperature.

The reaction mixture was heated at 50° C. for nine hours. Pentaerythritol 3.41 g (0.025 mole) and triethylamine 16.2 g (0.12 mole) were then added and the reaction mixture heated an additional nine hours at 55° to 80° C. under a stream of nitrogen. Then, solvent was distilled off, and 100 ml of benzene was added. The precipitated triethylamine hydrochloride was filtered and the benzene was evaporated.

The residual solid was recrystallized from benzene, and a white powder of m.p. 244° C. was obtained.

The phenolic antioxidant component of the stabilizer composition of the invention can be a liquid or a solid, and contains one or more phenolic hydroxyl groups, and one or more phenolic nuclei, and can contain from about eight to about three hundred carbon atoms, In addition, the phenolic nucleus can contain an oxy or thio ether group.

The alkyl-substituted phenols and polynuclear phenols, because of their molecular weight, have a higher boiling point and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatability with the liquid stabilizer system, and therefore there is no upper limit on the number of alkyl carbon atoms. Usually from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

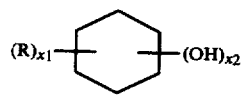

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl;

$x_1$ and $x_2$ are integers from one to four, and the sum of $x_1$ and $x_2$ does not exceed six.

The polycyclic phenol employed in the stabilizer combination is one having at least two aromatic nuclei linked by a polyvalent linking radical, as defined by the formula:

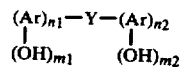

wherein:

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy $$(R'C-O) \atop \| \atop O$$

where R' is aryl, alkyl or cycloalkyl, or thiohydrocarbon groups having from one to about thirty carbon atoms, and carboxyl $$(-C-O-) \atop \| \atop O$$

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluorenyl groups.

When Ar is a benzene nucleus, the polyhydric polycyclic phenol has the structure:

[structure with $(OH)_{m1}$, $(OH)_{m2}$, $(OH)_{m3}$, $(R_1)_{x1}$, $(R_2)_{x2}$, $(R_3)_{x3}$, Y linkages, $y_1$, $y_2$]

wherein $R_1$, $R_2$ and $R_3$ are inert substituent groups as described in the previous paragraph;

$m_1$ and $m_3$ are integers from one to a maximum of five;

$m_2$ is an integer from one to a miximum of four;

$x_1$ and $x_3$ are integers from zero to four; and $x_2$ is an integer from zero to three;

$y_1$ is an integer from zero to about six; and $y_2$ is an integer from one to five, preferably one or two.

Preferably, the hydroxyl groups are located ortho and/or para to Y.

Exemplary Y groups are alkylene, alkylidene, and alkenylene arylene, alkylarylene, arylalkylene, cycloalkylene, cycloalkylidene, and oxa- and thia-substituted such groups; carbonyl groups, tetrahydrofuranes, esters and triazino groups. The Y groups are usually bi, tri, or tetravalent, connecting two, three or four Ar groups. However, higher valency Y groups, connecting more than four Ar groups can also be used. According to their constitution, the Y groups can be assigned to subgenera as follows:

(1) Y groups where at least one carbon in a chain or cyclic arrangement connect the aromatic groups, such as:

$-CH_2-CH_2-$; $-(CH_2)_5-$; $-CH_2-$; $-CH_2-\bigcirc-CH_2-$;

[additional cyclic structures]

-continued

[various alkyl and cyclic structures including $CH_3$, $C_2H_5$, $C_3H_7$, $C_4H_9$ substituted groups]

(2) Y groups made up of more than a single atom including both carbon and other atoms linking the aromatic nuclei, such as:

$-CH_2-O-CH_2-$; $-CH(CH_3)-CH_2-O-CH_2-CH(CH_3)-$;

$-O-CH_2-CH_2-O-$; $-CH_2-$[furan]$-CH_2-$;

$-CH_2-$[thiophene]$-CH_2-$; $-S-CH_2-S-$;

$-CH_2-$[thiophene]$-CH_2-$; $-\overset{O}{\overset{\|}{C}}-O-(CH_2)_4-O-\overset{O}{\overset{\|}{C}}-$;

$C[-CH_2OOCCH_2CH_2-]_4\equiv$;

$-CH_2CH_2-\overset{O}{\overset{\|}{C}}-O-CH_2CH_2-O-\overset{O}{\overset{\|}{C}}-CH_2CH_2-$;

-continued

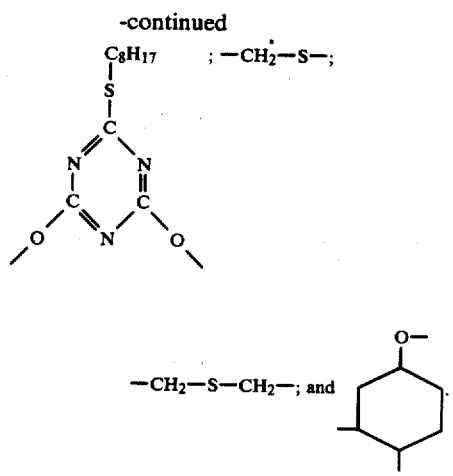

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2,6-di-t-butyl-4-sec-butylphenol, 2-t-butyl-4-methoxy phenol, 2,4-dinonyl phenol, 2,3,4,5-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl phenol, o-, and m-tert-butyl-p-hydroxy-anisole, p-n-decyloxy-phenol, p-n-decyloxy-cresol, nonyl-n-decyloxycresol, eugenol, isoeugenol, glyceryl monosalicylate, methyl-p-hydroxy-cinnamate, 4-benzyloxy-phenol, p-acetylaminophenol, p-stearylaminophenol, methyl-p-hydroxy benzoate, p-di-chloro-benzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl(4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butylresorcinol, 2,6-di-isopropyl-phloroglucinol.

Exemplary polyhydric polycyclic phenols are 2,2′-methylene bis(2,6-di-tertiary-butyl-phenol),2,2′-methylenebis (4-methyl-6-t-butylphenol),2,2′-ethylidenebis(4,6-di-t-butyl-phenol), 2,2-bis-(4-hydroxyphenyl)-propane, methylene bis (p-cresol), 4,4′benzylidene bis(2-tertiary-butyl-5-methy-phenol), 4,4′-cyclohexylidene bis(2-tertiary-butylphenol), 2,2′-methylene bis(4-methyl-6-(1′-methyl-cyclohexyl)phenol), 2,6-bis(2′-hydroxy-3′-tertiary-butyl-5′-methylbenzyl)-4-methylphenol, 4,4′-bis(2-tertiary-butyl-5-methyl-phenol), 2,2′-bis(4-hydroxy-phenyl)butane, ethylene bis(p-cresol), 2,2′-methylenebis(4-methyl-6-nonyl-phenol), 4,4′-isopropylidenebis(2,6-di-t-butylphenol), 4,4′-butylidene bis (2,6-di-t-butylphenol), 4,4′-butylidenebis(6-t-butyl-m-cresol), 1,1,3-tris(2-methyl-4-hydroxy-5-t-butylphenyl)butane, 2,6-bis (2-hydroxy-3-nonyl-5-methylbenzyl)-4-methylphenol, 4,4′-n-butylidene-(2-t-butyl-5-methylphenol), 2,2′-methylenebis(4-methyl-6-(1′-methyl-cyclohexyl)phenol), 4,4′-cyclohexylenebis (2-tertiary-butylphenol), 2,6-bis(2′-hydroxy-3′-t-butyl-5′-methyl benzyl)-4-methylphenol, 1,3′-bis(naphthalene-2,5-diol) propane, and 2,2′-butylenebis(naphthalene-2,7-diol), (3-methyl-5-tert-butyl-4-hydroxyphenyl)-4′-hydroxyphenyl)propane, 2,2′-methylenebis (4-methyl-5-isopropylphenol), 2,2′-methylenebis(5-tert-butyl-4-chlorophenol),(3,5-di-tert-butyl-4-hydroxyphenyl)-(4′-hydroxyphenyl)ethane, (2-hydroxyphenyl)-(3′,5′-di-tert-butyl-4′,4-hydroxyphenyl)ethane, 2,2′-methylenebis(4-octylphenol), 4,4′-propylene-bis(2-tert-butyl-phenol), 2,2′-isobutylenebis(4-nonylphenol), 2,4-bis(4-hydroxy-3-t-butylphenoxy)-6-(n-octylthio)-1,3,5-triazine, 2,4,6-tris(4-hydroxy-3-t-butylphenoxy)-1,3,5-triazine, 4,4′-bis(4-hydroxyphenyl)pentanoic acid octadecyl ester, cyclopentylene-4-4′-bisphenol, 2-ethylbutylene-4,4′-bisphenol, 4,4′-cyclooctylene-bis(2cyclohexylphenol),β,β-thiodiethanolbis(3-tert-butyl-4-hydroxy-phenoxy acetate),1,4-butanediolbis(3-tert-butyl-4-hydroxy phenoxy acetate), pentaerythritoltetra-(4-hydroxyphenol propionate), 2,4,4′-tri-hydroxy benzophenone, 4,4′-bis(4-hydroxyphenol) pentanoic acid octadecyl thiopropionate ester, 1,1,3-tris-(2′-methyl-4-hydroxy-5′-tert-butylphenyl)butane, 1,1,3-tris-(1-methyl-3-hydroxy-4-tert-butylphenyl)butane, 1,8-bis-(2-hydroxy-5-methylbenzoyl-n-octane, 1-methyl-3-(3-methyl-5-tert-butyl-4-hydroxy-benzyl)-naphthalene, 2,2′-(2-butene)-bis-(4-methoxy-6-tert-butyl phenol)-bis-[3,3-bis-(4-hydroxy-3-t-butylphenyl) butyric acid] glycol ester,4,4′-butylidene-bis-(6-t-butyl-m-cresol), 1,1,3-tris-(2-methyl-4-hydroxy-5-t-butylphenyl) butane, 1,3,5-tris-(3,5-di-t-butyl-4-hydroxybenzyl)-2,4,6-trimethylbenzene, tetrakis[methylene-3-(3,5-di-t-butyl-4-hydroxyphenyl) propionate] methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl) phenoxy-1,3,5-triazine, and pentaerythritol hydroxyphenyl propionate, thiodiglycolbis(3,5-di-t-butyl-4-hydroxyphenyl propionate), stearyl-3-(3,5-di-t-butyl-4-hydroxyphenyl)-propionate, bis(4-t-butyl-3-hydroxy-2,6-dimethylbenzylthio)terephthalate, distearyl(4-hydroxy-3-methyl-5-t-butyl)benzylmalonate, stearyl(3,5-dimethyl-4-hydroxybenzyl)thioglycolate, bis[3,3-bis(4-hydroxy-3-t-butylphenyl)butyric acid]glycolester, 4,4′-thiobis (6-t-butyl-m-cresol) and 1,3,5-tris(2,6-dimethyl-3-hydroxy-4-t-butylbenzyl)isocyanurate.

A particularly desirable class of polyhydric polycyclic phenols are the dicyclopentadiene polyphenols, which are of the type:

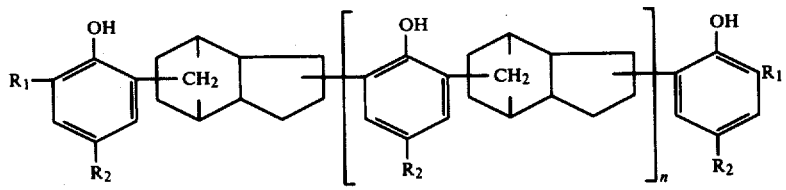

in which
R₁ and R₂ are lower alkyl, and can be the same or different, and
n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

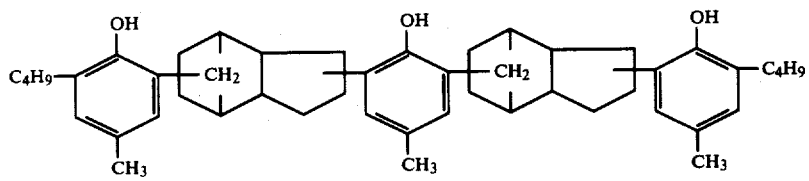

The polyhydric polycyclic phenols used in the invention can also be condensation products of phenol or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus (1). For method of preparation, see e.g., U.S. Pat. Nos. 3,124,555, 3,242,135 and British Pat. No. 961,504.

The phosphites and stabilizer compositions of the invention are especially effective in enhancing the resistance to deterioration by heat and light of polyvinyl chloride resins. The term "polyvinyl chloride" as used herein is inclusive of any polymer formed at least in part of the recurring group:

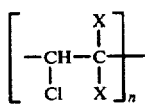

and having chlorine content in excess of 40%. In this group, the X groups can each be either hydrogen or chlorine, and n is the number of such units in the polymer chain. In polyvinyl chloride homopolymers, each of the X groups is hydrogen. Thus, the term includes not only polyvinyl chloride homopolymers but also after-chlorinated polyvinyl chlorides as a class, for example, those disclosed in British Pat. No. 893,288 and also copolymers of vinyl chloride in a major proportion and other copolymerizable monomers in a minor proportion, such as copolymers of vinyl chloride and vinyl acetate, copolymers of vinyl chloride with maleic or fumaric acids or esters, and copolymers of vinyl chloride with styrene. The stabilizer compositions are effective also with mixtures of polyvinyl chloride in a major proportion with a minor proportion of other synthetic resins such as chlorinated polyethylene or a copolymer of acrylonitrile, butadiene and styrene.

The phosphites and stabilizer compositions are applicable to the stabilization of rigid polyvinyl chloride resin compositions, that is, resin compositions which are formulated to withstand high processing temperatures, of the order of 375° F. and higher, as well as plasticized polyvinyl chloride resin compositions of conventional formulation, even though resistance to heat distortion is not a requisite. Conventional plasticizers well known to those skilled in the art can be employed, such as, for example, dioctyl phthalate, octyl diphenyl phosphate and epoxidized soybean oil.

Particularly useful plasticizers are the epoxy higher esters having from 20 to 150 carbon atoms. Such esters will initially have had unsaturation in the alcohol or acid portion of the molecule, which is taken up by the formation of the epoxy group.

Typical unsaturated acids are acrylic, oleic, linoleic, linolenic, erucic, ricinoleic, and brassidic acids, and these may be esterified with organic monohydric or polyhydric alcohols, the total number of carbon atoms of the acid and the alcohol being within the range stated. Typical monohydric alcohols include butyl alcohol, 2-ethyl hexyl alcohol, lauryl alcohol, isooctyl alcohol, stearyl alcohol, and oleyl alcohol. The octyl alcohols are preferred. Typical polyhydric alcohols include pentaerythritol, glycerol, ethylene glycol, 1,2-propylene glycol, 1,4-butylene glycol, neopentyl glycol, ricinoleyl alcohol, erythritol, mannitol and sorbitol. Glycerol is preferred. These alcohols may be fully or partially esterified with the epoxidized acid. Also useful are the epoxidized mixtures of higher fatty acid esters found in naturally-occurring oils such as epoxidized soybean oil, epoxidized olive oil, epoxidized coconut oil, epoxidized cotton-seed oil, epoxidized tall oil fatty acid esters and epoxidized tallow. Of these, epoxidized soybean oil is preferred.

The alcohol can contain the epoxy group and have a long or short chain, and the acid can have a short or long chain, such as epoxystearyl acetate, epoxystearyl stearate, glycidyl stearate, and polymerized glycidyl methacrylate.

The polyvinyl chloride resin can be in any physical form, including, for example, powders, films, sheets, molded articles, foams, filaments and yarns.

A sufficient amount of the phosphite and stabilizer composition is used to enhance the resistance of the polyvinyl chloride to deterioration in physical properties, including, for example, discoloration and embrittlement, under the heat and/or light conditions to which the polymer will be subjected. Very small amounts are usually adequate. Amounts within the range from about 0.01 to about 5% of the phosphite and from about 0.01 to about 10% of the stabilizer composition by weight of the polyvinyl chloride resin are satisfactory. Preferably, an amount within the range from about 0.05 to about 2% of phosphite, and from about 0.1 to about 5% of stabilizer composition, is employed for optimum stabilizing effectiveness.

The phosphites and stabilizer compositions of the invention can be employed as the sole stabilizers. They can also be used in combination with other conventional heat and light stabilizers for polyvinyl chloride resins, such as, for example, polyvalent metal salts and alkaline earth metal phenolates, as well as epoxy compounds.

A particularly useful stabilizer system contains the following amounts of ingredients:
(a) phosphite in an amount within the range from about 25 to about 45 parts by weight;
(b) phenolic antioxidant in an amount within the range from about 0.01 to about 1 part by weight;
(c) polyvalent metal salt of an aliphatic carboxylic acid or of an alkyl phenol in an amount within the range from about 25 to about 45 parts by weight;
plus any one or more of the following optional ingredients:
(d) free aliphatic carboxylic acid in an amount within the range from about 0.5 to about 5 parts by weight, but in no case more than 15% by weight of the cadmium carboxylate; and
(e) acid phosphite in an amount within the range from about 0.5 to about 5 parts by weight.

In addition, any of the conventional polyvinyl chloride resin additives, such as lubricants, emulsifiers, antistatic agents, flame-proofing agents, pigments and fillers, can be employed.

Preferably, the stabilizer system is added to the polyvinyl chloride resin in an amount to provide in the resin from about 0.2 to about 1% of the phosphite; from about 0.1 to about 2% of phenolic antioxidant; and from about 0 to about 1% total of one or more of the additional ingredients, as noted above.

The stabilizer system is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polyvinyl chloride resin can be worked into the desired shape, such as by milling, calendering, extrusion or injection molding, or fiber-forming. In such operations, it will be found to have a considerably improved resistance to discoloration and embrittlement on exposure to heat and light.

The phosphites and stabilizer compositions of the invention are especially effective heat stabilizers for olefin polymers such as polyethylene, polypropylene, polybutylene, polypentylene, polyisopentylene, and higher polyolefins.

Olefin polymers on exposure to elevated temperatures undergo degradation, resulting in embrittlement and discoloration.

The phosphites and stabilizer compositions can be employed with any olefin polymer, including low-density polyethylene, high density polyethylene, polyethylenes prepared by the Ziegler-Natta process, polypropylenes prepared by the Ziegler-Natta process, and by other polymerization methods from propylene, poly(butene-1)poly(pentene-1)poly(3-methylbutene-1)poly(4-methylpentene-1), polystyrene, and mixtures of polyethylene and polypropylene with other compatible polymers, such as mixtures of polyethylene and polypropylene, and copolymers of such olefins, such as copolymers of ethylene, propylene, and butene, with each other and with other copolymerizable monomers. The term "olefin polymer" encompasses both homopolymers and copolymers.

Polypropylene solid polymer can be defined in a manner to differentiate it from other polyolefins as having a density within the range from 0.86 to 0.91, and a melting point about 150° C. The phosphites of the invention are applicable to all such polypropylenes, as distinguished from polypropylenes in the liquid form or in semi-liquid of gel-like forms, such as are used as greases and waxes.

The phosphites and stabilizer compositions of the invention are applicable to polypropylenes prepared by any of the various procedures, for the molecular weight and tacticity are not factors affecting this stabilizer system. Isotactic polypropylene, available commercially under the trade name PRO-FAX, and having a softening or hot-working temperature of about 350° F., is an example of a sterically regular polypropylene polymer.

Mixtures of polypropylene with other compatible polymers and copolymers of propylene with copolymerizable monomers not reactive with the phosphites or stabilizer composition can also be stabilized, for example, mixtures of polyethylene and polypropylene, and copolymers of propylene and ethylene stabilizer.

The phosphites and stabilizer compositions are also effective to enhance the resistance to heat degradation of polystyrene; polydienes, such as polybutadiene and polyisoprene; and copolymers of olefins and dienes with other ethylenically and acetylenically unsaturated monomers, such as ethylene-vinyl acetate copolymers, styrene-butadiene copolymers, acrylonitrile-styrene-butadiene copolymers, synthetic rubbers of all types, such as polychloroprene; polyvinylidene chloride; and copolymers of vinyl chloride and vinylidene chloride; vinylidene chloride and vinyl acetate; and other ethylenically unsaturated monomers; polyacetals such as polyoxymethylene and polyoxyethylene; polycarbonates; polyphenylene oxides; polyesters such as polyethylene glycol-terephthalic acid ester polymers; polyamides such as poly-epsilon-caprolactam; polyhexamethylene adipamide and polydecamethylene adipamide; polyurethanes; and epoxy resins.

The synthetic polymer can be in any physical form, including (for example) filaments, yarns, films, sheets, molded articles, latex and foam.

A sufficient amount of the stabilizer composition including the phosphite and phenolic antioxidant is used to improve the resistance of the synthetic polymer to deterioration in physical properties, including, for example, discoloration, reduction in melt viscosity and embrittlement, under the conditions to which the polymer will be subjected. Very small amounts are usually adequate. Amounts within the range from about 0.001 to about 5% total stabilizers by weight of the polymer are satisfactory. Preferably, from 0.01 to 3% is employed, for optimum stabilization.

The stabilizer compositions of the invention can be employed as the sole stabilizers or in combination with other conventional heat and light stabilizers for the particular olefin polymer.

Thus, for example, there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salt of divalent manganese can be used.

With synthetic rubbers and acrylonitrile-butadiene-styrene terpolymers, polyvalent metal salts of higher fatty acids can be used.

In addition, other conventional additives for synthetic polymers, such as plasticizers, lubricants, emulsifiers, antistatic agents, flame-proofing agents, pigments and fillers, can be employed.

The stabilizer composition is incorporated in the polymer in suitable mixing equipment, such as a mill or a Banbury mixer. If the polymer has a melt viscosity with is too high for the desired use, the polymer can be worked until its melt viscosity has been reduced to the desired range before addition of the stabilizers. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples illustrate preferred stabilizer compositions and resin compositions of the invention:

EXAMPLES 1 to 3

A group of cis-1,4-polyisoprene compositions was prepared, having the following formulation:

| Ingredient | Parts by Weight |
|---|---|
| Poly-cis-1,4-isoprene (Mol. weight 680,000) | 100 |
| Pentaerythritol tetrakis (3,5-di-tert-butyl-4-hydroxyphenyl) propionate | 0.1 |
| Phosphite shown in Table I | 0.2 |

The cis-1,4-polyisoprene, pentaerythritol tetrakis (3,5-di-t-butyl-4-hydroxyphenyl propionate) and phosphite were dissolved in 250 ml of isooctane, and the isooctane was then distilled off. This polyisoprene composition was heated at 100° C. in a Geer oven for three hours and color of the composition was observed, and the inherent viscosity in toluene solution before and after the heating was measured.

The results are shown in Table I.

TABLE I

| Example No. | Phosphite | Color of composition | Inherent viscosity Original | Inherent viscosity After Heating |
|---|---|---|---|---|
| Control | | | | |
| 1 | None | Brown | 4.7 | — |
| 2 | Tris(2,4-di-t-butylphenyl) phosphite | Pale Brown | 4.6 | 3.9 |
| 3 | Bis(2,4-di-t-butyl-phenyl) pentaerythritol diphosphite | Yellow | 4.5 | 3.7 |
| Example | | | | |
| 1 | 2,6-Di-t-butyl-4-methylphenyl phenylpentaerythritol diphosphite | Colorless | 4.6 | 4.4 |
| 2 | 2,6-Di-t-butyl-4-methylphenyl isooctylpentaerythritol diphosphite | Colorless | 4.7 | 4.4 |
| 3 | Bis(2,6-di-t-butyl-4-methylphenyl)pentaerythritol diphosphite | Colorless | 4.8 | 4.5 |

It is apparent from Controls 1, 2 and 3 that in combination with phenolic antioxidant, the phosphites in accordance with the invention give a considerable improvement in effectiveness as compared to the phosphites in the combinations of the Controls.

EXAMPLES 4 to 8

Acrylonitrile-styrene copolymer resin compositions were prepared using stabilizer compositions of the invention and having the following formulation:

| Ingredient | Parts by Weight |
|---|---|
| Acrylonitrile-styrene copolymer | 100 |
| 1,3,5-Tris(2,6-dimethyl-3-hydroxybutyl benzyl) isocyanurate | 0.05 |
| Phosphite as shown in Table II | 0.05 |

The stabilizers were blended with the resin on a two-roll mill, and extruded at 230° C. Samples were prepared by injection molding of the resulting blend, and yellowness measured in a Hunter color difference meter.

Samples were heated at 230° C. for ten minutes before molding, and yellowness again measured in a Hunter color difference meter. Samples were also heated at 230° C. for twenty minutes, and yellowness measured in the same way.

The results are shown in Table II:

TABLE II

| Example No. | Phosphite | Yellowness Original | Yellowness After 10 Minutes | Yellowness After 20 Minutes |
|---|---|---|---|---|
| Control | | | | |
| 1 | Bis(2,4-di-t-butyl-5-methylphenyl) pentaerythritol diphosphite | 15 | 20 | 33 |
| 2 | Bis(2,6-di-t-butylphenyl) pentaerylthritol diphosphite | 18 | 22 | 36 |

TABLE II-continued

| Example No. | Phosphite | Yellowness Original | After 10 Minutes | After 20 Minutes |
|---|---|---|---|---|
| Example | | | | |
| 4 | Bis(2,6-di-t-butyl-4-methylphenyl) pentaerythritol diphosphite | 12 | 14 | 18 |
| 5 | Bis(2,6-di-t-butyl-4-ethylphenyl) pentaerythritol diphosphite | 11 | 13 | 17 |
| 6 | 2,6-Di-t-buty-4-methylphenyl cyclohexyl pentaerythritol diphosphite | 10 | 12 | 15 |
| 7 | 2,6-Di-t-butyl-4-methylphenyl tridecyl pentaerythritol diphosphite | 10 | 12 | 15 |
| 8 | 2,6-Di-t-butyl-4-mehtylphenyl 2-cyclohexylphenyl pentaerythritol diphosphite | 12 | 15 | 19 |

It is apparent from the data that the phosphites of the invention are far superior to the phosphites of the Controls.

EXAMPLES 9 to 13

Acrylonitrile-butadiene-styrene terpolymer resin compositions were prepared using stabilizer compositions of the invention and having the following formulation:

| Ingredient | Parts by Weight |
|---|---|
| Acrylonitrile-butadiene-styrene terpolymer | 100 |
| Calcium stearate | 1.0 |
| 1,3,5-Tris-(3,5-di-t-butyl-4-hydroxy benzyl) isocyanurate | 0.1 |
| Phosphite as shown in Table III | 0.3 |

The stabilizers were blended with the resin on a two-roll mill and extruded at 200° C., followed by injection molding at 230° C. of the resulting blend, to prepare samples.

Heat stability was evaluated by heating the specimen samples at 135° C. in a Geer oven for thirty hours. The whiteness of the specimens was evaluated using a Hunter color difference meter. Izod impact strength of the specimens was determined before and after immersion in hot water at 100° C. for seventy-two hours.

The results are shown in Table III.

TABLE III

| Example No. | Phosphite | Whiteness | Izod impact strength (kg. cm/cm) Original | After Heating | After Immersion |
|---|---|---|---|---|---|
| Control | | | | | |
| 1 | Bis(2,4-di-t-butyl-6-methylphenyl)pentaerythritol diphosphite | 17.6 | 13.3 | | 13.5 |
| Example | | | | | |
| 9 | 2,6-Di-t-butyl-4-methylphenyl isooctyl pentaerythritol diphosphite | 18.7 | 17.2 | | 17.6 |
| 10 | 2,6-Di-t-butyl-4-methylphenyl stearyl pentaerythritol diphosphite | 19.2 | 17.5 | | 17.8 |
| 11 | 2,6-Di-t-butyl-4-methylphenyl benzyl pentaerythritol diphosphite | 18.0 | 16.9 | | 16.2 |
| 12 | Bis(2,6-di-t-butyl-4-methylphenyl pentaerythritol diphosphite | 18.5 | 17.2 | | 16.7 |
| 13 | 2,6-Di-t-butyl-4-methylphenyl nonylphenyl pentaerythritol diphosphite | 18.4 | 17.0 | | 16.5 |

It is apparent from the data that in the stabilizer compositions of the invention, the phosphites of the invention are far superior to the Control.

EXAMPLES 14 to 19

Polypropylene compositions were prepared using stabilizer compositions of the invention and having the following formulation:

| Ingredient | Parts by Weight |
|---|---|
| Polyproplyene (Profax 6501) | 100 |
| Ca stearate | 0.2 |
| Dilauryl thiodipropionate | 0.2 |
| Pentaerythritol tetrakis(3,5-di-t-butyl-4-hydroxyphenyl) propionate | 0.1 |
| Phosphite as shown in Table IV | 0.1 |

The composition was thoroughly blended for five minutes in a Brabender Plastograph.

One part of the mixture was then extruded at 20 rpm, cylinder temperature 230° to 240° C. and head die temperature 250° C. Another part was injection molded at 475 kg/cm², cylinder temperature 240° C., nozzle temperature 250° C., to form sheets 95×40×1 mm.

Pieces 2.5 cm² were cut off from the sheets and heated at 160° C. in a Geer oven to evaluate heat stability.

The time in hours required for the sheet to develop a noticeable discoloration and/or embrittlement was noted as the hours to failure.

The yellowness of the sheet after exposure to ultraviolet light for 72 hours was measured in a Hunter color difference meter.

The results obtained are shown in Table IV.

TABLE IV

| Example No. | Phosphite | Hours to failure | Yellowness (%) Original | After 72 hours |
|---|---|---|---|---|
| Control | Bis(2,6-di-t-butylphenyl) pentaerythritol diphosphite | 538 | 9.0 | 11.2 |
| Example | | | | |
| 14 | Bis(2,6-di-t-butyl-4-methylphenyl) pentaerythritol diphosphite | 685 | 7.8 | 9.1 |
| 15 | Bis(2,6-di-t-butyl-4-ethyl- | 638 | 7.9 | 9.5 |

TABLE IV-continued

| Example No. | Phosphite | Hours to failure | Yellowness (%) Orig-inal | Yellowness (%) After 72 hours |
|---|---|---|---|---|
| | phenyl) pentaerythritol diphosphite | | | |
| 16 | 2,6-Di-t-butyl-4-methylphenyl butylcarbitol pentaerythritol diphosphite | 653 | 7.7 | 9.2 |
| 17 | 2,6-Di-t-butyl-4-methylphenyl butyltriglycol pentaerythritol diphosphite | 703 | 7.9 | 9.5 |
| 18 | 2,6-Di-t-butyl-4-ethylphenyl isodecyl pentaerythritol diphosphite | 684 | 7.8 | 9.4 |
| 19 | 2,6-Di-t-butyl-4-ethylphenyl-4-t-butylphenyl pentaerythritol diphosphite | 712 | 7.6 | 9.3 |

It is apparent from the above results that in the stabilizer compositions of the invention the phosphites are superior to the Control in enhancing resistance of the polypropylene polymer composition to deterioration when heated and when exposed to ultraviolet light.

EXAMPLES 20 TO 30

Polypropylene compositions were prepared using stabilizer compositions of the invention with a variety of phenolic antioxidants, and having the following formulation:

| Ingredient | Parts by Weight |
|---|---|
| Polypropylene (Profax 6501) | 100 |
| Ca stearate | 0.2 |
| Dilauryl thiodipropionate | 0.2 |
| Bis(2,6-di-t-butyl-4-methylphenyl)pentaerythritol diphosphite | 0.1 |
| Phenolic antioxidant as shown in Table V | 0.1 |

The composition was thoroughly blended for five minutes in a Brabender Plastograph.

One part of the mixture was then extruded at 20 rpm, cylinder temperature 230° to 240° C. and head die temperature 250° C. Another part was injection-molded at 475 kg/cm², cylinder temperature 240° C., nozzle temperature 250° C., to form sheets 95×40×1 mm.

Pieces 2.5 cm² were cut off from the sheets and heated at 160° C. in a Geer oven to evaluate heat stability.

The time in hours required for the sheets to develop a noticeable discoloration and/or embrittlement was noted as the hours to failure.

The yellowness of the sheet after exposure to ultraviolet light for 72 hours was measured in a Hunter color difference meter.

The results obtained are shown in Table V.

TABLE V

| Example No. | Phenolic Antioxidant | Heat Stability (hours) | Yellowness (%) Orig-inal | Yellowness (%) After 72 hours |
|---|---|---|---|---|
| Control | None | 24 | 12.3 | — |
| Example | | | | |
| 20 | 2,6-Di-t-butyl-4-methylphenol | 96 | 10.3 | 15.2 |
| 21 | 4,4'-Butylidenebis(2-t-butyl-5-methylphenol) | 183 | 9.7 | 12.7 |
| 22 | 1,1,3-tris(2-methyl-4-hydroxy-5-t-butylphenyl)butane | 216 | 9.8 | 12.4 |
| 23 | 1,3,5-Trimethyl-2,4,6-tris(3,5-di-t-butyl-4-hydroxybenzyl)benzene | 335 | 9.1 | 11.6 |
| 24 | Stearyl-3,5-di-t-butyl-4-hydroxyphenyl propionate | 642 | 7.7 | 9.3 |
| 25 | Thiodiethylene glycolbis(3,5-di-t-butyl-4-hydroxyphenyl)propionate | 628 | 8.2 | 9.9 |
| 26 | 1,6-Hexanediolbis(3,5-di-t-butyl-4-hydroxyphenyl propionate) | 620 | 7.8 | 9.6 |
| 27 | 1,3,5-Tris(2-hydroxyethyl) isocyanurate tris(3,5-di-t-butyl-4-hydroxyphenyl propionate) | 674 | 8.0 | 9.2 |
| 28 | Pentaerythritol tetrakis (3,5-di-t-butyl-4-hydroxyphenyl propionate) | 685 | 7.8 | 9.1 |
| 29 | 1,3,5-Tris(3,5-di-t-butyl-4-hydroxybenzyl)isocyanurate | 716 | 7.6 | 9.0 |
| 30 | 1,3,5-Tris(2,6-dimethyl-4-t-butyl-3-hydroxybenzyl) isocyanurate | 650 | 7.8 | 9.3 |

It is apparent from the above data that the phenolic antioxidants appreciably improve the effectiveness of the phosphite Control.

EXAMPLES 31 TO 35

High density polyethylene compositions were prepared using stabilizer compositions of the invention, and having the following formulation:

| Ingredient | Parts by Weight |
|---|---|
| High-density polyethylene (Hizex 5100E) | 100 |
| Distearyl thiodipropionate | 0.3 |
| Stearyl 3,5-di-t-butyl-4-hydroxyphenyl propionate | 0.1 |
| Phosphite as shown in Table VI | 0.1 |

The stabilizers were blended with the polymer on a two-roll mill at 150° C. for five minutes, and sheets 1 mm thick were prepared by compression molding of the blend at 150° C. and 180 kg/cm² pressure.

Pieces 10×20 mm were cut off from the sheets, and heated at 150° C. in a Geer oven on aluminum foil.

The time in hours when degradation set in, as determined by a significant discoloration and/or embrittlement, was noted as hours to failure.

The results are reported in Table VI.

TABLE VI

| Phosphite | Hours to Failure |
|---|---|
| Example No. | |
| Control   Bis(2-t-butyl-4,6-dimethylphenyl) pentaerythritol diphosphite | 523 |
| Example | |
| 31   Bis(2,6-di-t-butyl-4-methylphenyl) pentaerythritol diphosphite | 683 |
| 32   2,6-Di—t-butyl-4-methylphenyl isotridecyl pentaerythritol diphosphite | 675 |
| 33   2,6-Di—t-butyl-4-methylphenyl-2-ethylhexyl pentaerythritol diphosphite | 702 |

TABLE VI-continued

|  | Phosphite | Hours to Failure |
|---|---|---|
| 34 | 2,6-Di—t-butyl-4-ethylphenyl dinonylphenyl pentaerythritol diphosphite | 648 |
| 35 | 2,6-Di—t-butyl-4-ethylphenyl-4-t-octylphenyl pentaerythritol diphosphite | 650 |

It is apparent from the above results that the phosphites of the invention are superior to the Control phosphite in enhancing the resistance of the polyethylene polymer composition to deterioration when exposed to heat.

EXAMPLES 36 TO 40

Resin compositions having the following composition were prepared:

| Ingredient | Parts by Weight |
|---|---|
| Poly(2,6-dimethyl-1,4-phenyleneoxide) | 50 |
| Polystyrene | 47.5 |
| Polycarbonate | 2.5 |
| TiO$_2$ | 3 |
| Phosphite as shown in Table VII | 0.5 |

The ingredients were mixed and then extruded at 60 rpm, 260° C., followed by injection molding at 290° C. to prepare the test pieces. The heat stability was evaluated by heating the test pieces in a Geer oven at 125° C. for 100 hours. Elongation and Izod impact strength were measured before and after the heating, and the percent elongation and percent Izod impact strength retained were calculated.

The results are shown in Table VII.

TABLE VII

|  | Phosphite | % Elongation Retained | % Izod Impact Strength Retained |
|---|---|---|---|
| Example No. |  |  |  |
| Control | Bis(2,4-di-t-butyl-6-methylphenyl)pentaerythritol diphosphite | 40 | 53 |
| Example |  |  |  |
| 36 | Bis(2,6-di-t-butyl-4-methylphenyl)pentaerythritol diphosphite | 58 | 71 |
| 37 | 2,6-Di—t-butyl-4-methylphenyl-2,4-di-t-butylphenyl pentaerythritol diphosphite | 52 | 69 |
| 38 | 2,6-Di—t-butyl-4-methylphenyl lauryl pentaerythritol diphosphite | 54 | 75 |
| 39 | 2,6-Di—t-butyl-4-ethylphenyl-2-phenylphenyl pentaerythritol diphosphite | 50 | 68 |
| 40 | 2,6-Di—t-butyl-4-ethylphenyl oleyl pentaerythritol diphosphite | 54 | 70 |

The phosphites of the invention are clearly more effective heat stabilizers than the Control phosphite.

EXAMPLES 41 TO 43

Polycarbonate resin compositions were prepared having the following formulation:

| Ingredient | Parts by Weight |
|---|---|
| Polycarbonate | 100 |
| Phosphite as shown in Table VIII | 0.2 |

The ingredients were mixed and compression-molded at 260° C. to prepare a sheet 1 mm thick. Heat stability was evaluated by heating the sheets in a Geer oven at 230° C. for thirty minutes, and then observing the color of the sheets.

The results are shown in Table VIII

TABLE VIII

|  | Phosphite | Color of Sheet |
|---|---|---|
| Example No. |  |  |
| Control | Bis(2,4-di-t-butylphenyl) pentaerythritol diphosphite | Yellow |
| Example |  |  |
| 41 | Bis(2,6-di-t-butyl-4-methylphenyl) pentaerythritol diphosphite | Colorless |
| 42 | Bis(2,6-di-t-butyl-4-ethylphenyl) pentaerythritol diphosphite | Colorless |
| 43 | 2,6-Di—t-butyl-4-methylphenyl isodecyl pentaerythritol diphosphite | Colorless |

The phosphites of the invention are clearly more effective heat stabilizers than the Control phosphite.

Having regard to the foregoing disclosure, the following is claimed as inventive and patentable embodiments thereof:

1. 2,6-Di-tertiary butyl phenyl pentaerythritol spiro bis-phosphites having the structure:

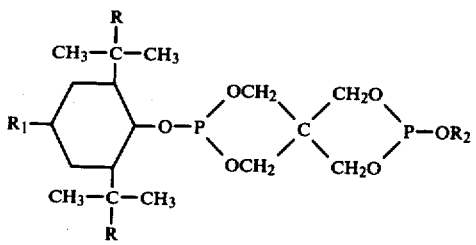

wherein:

R is alkyl having from one to six carbon atoms;
R$_1$ is methyl or ethyl; and
R$_2$ is selected from the group consisting of alkyl having from one up to about eighteen carbon atoms; cycloalkyl having from three up to about twelve carbon atoms; and alkaryl and aryl having from six to about thirty carbon atoms; such groups substituted with from one to about four oxy ether-O- and/or carboxylic ester-COO-groups; the residue of a polyhydric alcohol having from two to about eighteen carbon atoms, and from two to about ten hydroxyl groups; and the residue of a polyphenol having from six to about eighteen carbon atoms and from two to about ten phenolic hydroxyl groups.

2. 2,6-Di-tertiary butyl phenyl pentaerythritol spiro bis-phosphites according to claim 1 in which the R is methyl.

3. 2,6-Di-tertiary butyl phenyl pentaerythritol spiro bis-phosphtes according to claim 1 in which R is ethyl.

4. 2,6-Di-tertiary butyl phenyl pentaerythritol spiro bis-phosphites according to claim 1 in which $R_1$ is methyl.

5. 2,6-Di-tertiary butyl phenyl pentaerythritol spiro bis-phosphites according to claim 1 in which $R_2$ is alkyl.

6. 2,6-Di-tertiary butyl phenyl pentaerythritol spiro bis-phosphites according to claim 1 in which $R_2$ is alkyl substituted with oxyether-O-.

7. 2,6-Di-tertiary butyl phenyl pentaerythritol spiro bis-phosphites according to claim 1 in which $R_2$ is alkyl substituted with carboxylic ester COO—.

8. 2,6-Di-tertiary butyl phenyl pentaerythritol spiro bis-phosphites according to claim 1 in which $R_2$ is cycloalkyl.

9. 2,6-Di-tertiary butyl phenyl pentaerythritol spiro bis-phosphites according to claim 1 in which $R_2$ is aryl.

10. 2,6-Di-tertiary butyl phenyl pentaerythritol spiro bis-phosphites according to claim 1 in which $R_2$ is alkaryl.

11. 2,6-Di-tertiary butyl phenyl pentaerythritol spiro bis-phosphites according to claim 1 in which $R_2$ is the residue of a polyhydric alcohol.

12. 2,6-Di-tertiary butyl phenyl pentaerythritol spiro bis-phosphites according to claim 1 in which $R_2$ is the residue of a polyphenol.

13. 2,6-Di-tertiary butyl phenyl pentaerythritol spiro bis-phosphites according to claim 1 in which R and $R_1$ are each methyl and $R_2$ is alkyl.

14. A compound according to claim 1 in which R and $R_1$ are each methyl and $R_2$ is the residue of a polyhydric alcohol.

15. A compound according to claim 1 in which R and $R_1$ are each methyl and $R_2$ is the residue of a polyphenol.

16. A compound according to claim 1, bis(2,6-di-t-butyl-4-methylphenyl)-pentaerythritol diphosphite.

17. A compound according to claim 1, 2,6-di-t-butyl-4-methylphenyl-iso tridecyl pentaerythritol diphosphite.

18. A compound according to claim 1, 2,6-di-t-butyl-4-ethylphenyl-2-ethylhexyl pentaerythritol diphosphite.

19. A compound according to claim 1, bis(2,6-di-t-butyl-4-ethylphenyl) pentaerythritol diphosphite.

20. A compound according to claim 1, 2,6-di-t-butyl-4-methylphenyl-2-cyclohexylphenyl pentaerythritol diphosphite.

21. A stabilizer composition capable of enhancing resistance to deterioration by heat and/or light of synthetic resin compositions comprising a phenolic antioxidant and a phosphite according to claim 1.

22. A stabilizer composition according to claim 21 in which the phenolic antioxidant has the formula:

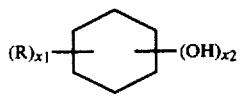

wherein:
R is selected from the group consisting of hydrogen; halogen; and organic radicals containing from one to about thirty carbon atoms; and
$x_1$ and $x_2$ are integers from one to four, and the sum of $x_1$ and $x_2$ does not exceed six.

23. A stabilizer composition according to claim 21 in which the phenolic antioxidant has the formula:

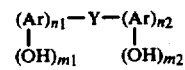

wherein:
Y is a polyvalent linking group selected from the group consisting of oxygen; carbonyl; sulfur; sulfinyl; and aromatic, aliphatic and cycloaliphatic hydrocarbon groups and oxyhydrocarbon, thiohydrocarbon and heterocyclic groups having from one up to twenty carbon atoms;
Ar is a phenolic nucleus having at least one up to five free phenolic hydroxyl groups; and
$m_1$ and $m_2$ are numbers from one to five, and $n_1$ and $n_2$ are numbers from one to four.

24. A stabilizer composition according to claim 21 in which the phenolic antioxidant has the formula:

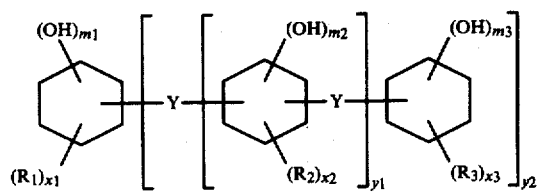

wherein:
$R_1$, $R_2$ and $R_3$ are inert substituent groups selected from the group consisting of halogen, alkyl, aryl, alkaryl, aralkyl, cycloalkenyl, cycloalkyl, alkoxy, aryloxy and acyloxy

where R' is aryl, alkyl or cycloalkyl containing from one to about thirty carbon atoms; thiohydrocarbon groups having from one to about thirty carbon atoms, and carboxyl

groups;
$m_1$ and $m_3$ are integers from one to a maximum of five;
$m_2$ is an integer from one to a maximum of four;
$x_1$ and $x_3$ are integers from zero to four; and
$x_2$ is an integer from zero to three;
$y_1$ is an integer from zero to about six; and
$y_2$ is an integer from one to five.

25. A stabilizer composition according to claim 21 in which the phenolic antioxidant is pentaerythritol tetrakis(3,5-t-butyl-4-hydroxyphenyl propionate).

26. A stabilizer composition according to claim 21 in which the phenolic antioxidant is 1,3,5-tris(2,6-dimethyl-3-hydroxy-4-t-butylbenzyl) isocyanurate.

27. A stabilizer composition according to claim 21 in which the phenolic antioxidant is 1,3,5-tris(3,5-di-t-butyl-4-hydroxybenzyl) isocyanurate.

28. A stabilizer composition according to claim 21 in which the phenolic antioxidant is 1,3,5-tris(2-hydroxyethyl) isocyanurate-tris(3,5-di-t-butyl-hydroxyphenyl propionate).

29. A stabilizer composition according to claim 21 in which the phenolic antioxidant is stearyl-3,5-di-t-butyl-4-hydroxyphenyl propionate.

30. A polyvinyl chloride resin composition having improved resistance to deterioration when heated at 350° F., comprising a polyvinyl chloride resin formed at least in part of the recurring group

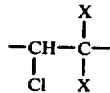

and having a chlorine content in excess of 40%, where X is either hydrogen or chlorine; and a phosphite in accordance with claim 1.

31. A polyvinyl chloride resin composition in accordance with claim 30 in which the polyvinyl chloride resin is polyvinyl chloride homopolymer.

32. A polyvinyl chloride resin composition in accordance with claim 30 in which the polyvinyl chloride resin is a copolymer of vinyl chloride and vinyl acetate.

33. An olefin polymer composition having improved resistance to deterioration comprising an olefin polymer selected from the group consisting of polymers of alpha-olefins having from two to six carbon atoms and polystyrene, and a phosphite in accordance with claim 1.

34. An olefin polymer composition in accordance with claim 33 wherein the polyolefin is polypropylene.

35. An olefin polymer composition in accordance with claim 33 wherein the polyolefin is polyethylene.

36. A cis-1,4-polyisoprene polymer composition comprising a cis-1,4-polyisoprene polymer and a phosphite in accordance with claim 1.

37. An acrylonitrile-butadiene-styrene terpolymer having improved resistance to deterioration comprising acrylonitrile-butadiene-styrene terpolymer and a phosphite in accordance with claim 1.

38. An acrylonitrile-styrene copolymer composition having improved resistance to deterioration comprising acrylonitrile-styrene copolymer and a phosphite in accordance with claim 1.

39. A polycarbonate resin composition having improved resistance to deterioration comprising a polycarbonate resin and a phosphite in accordance with claim 1.

40. A mixed polyphenylene-oxide-polystyrenepolycarbonate polymer composition having improved resistance to deterioration comprising polyphenylene oxide, polystyrene, polycarbonate, and a phosphite in accordance with claim 1.

41. A polyvinyl chloride resin composition having improved resistance to deterioration when heated at 350° F., comprising a polyvinyl chloride resin formed at least in part of the recurring group

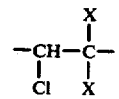

and having a chlorine content in excess of 40%, where X is either hydrogen or chlorine; and a stabilizer composition in accordance with claim 21.

42. A polyvinyl chloride resin composition in accordance with claim 21 in which the polyvinyl chloride resin is polyvinyl chloride homopolymer.

43. A polyvinyl chloride resin composition in accordance with claim 41 in which the polyvinyl chloride resin is a copolymer of vinyl chloride and vinyl acetate.

44. An olefin polymer composition having improved resistance to deterioration comprising an olefin polymer selected from the group consisting of polymers of alpha-olefins having from two to six carbon atoms and polystyrene, and a stabilizer composition in accordance with claim 21.

45. An olefin polymer composition in accordance with claim 44 wherein the polyolefin is polypropylene.

46. An olefin polymer composition in accordance with claim 44 wherein the polyolefin is polyethylene.

47. A cis 1,4-polyisoprene polymer composition comprising a cis-1,4-polyisoprene polymer and a phosphite in accordance with claim 1.

48. An acrylonitrile-butadiene-styrene terpolymer having improved resistance to deterioration comprising acrylonitrile-butadiene-styrene terpolymer and a stabilizer composition in accordance with claim 21.

49. An acrylonitrile-styrene copolymer composition having improved resistance to deterioration comprising acrylonitrile-styrene copolymer and a stabilizer composition in accordance with claim 21.

50. A polycarbonate resin composition having improved resistance to deterioration comprising a polycarbonate resin and a stabilizer composition in accordance with claim 21.

51. A mixed polyphenylene-oxide-polystyrene-polycarbonate-polymer composition having improved resistance to deterioration comprising polyphenylene oxide, polystyrene, polycarbonate and a stabilizer composition in accordance with claim 21.

* * * * *